(12) United States Patent
Laine et al.

(10) Patent No.: US 7,767,691 B2
(45) Date of Patent: Aug. 3, 2010

(54) MUSCARINIC ACETYLCHOLINE RECEPTOR ANTAGONISTS CONTAINING AN AZONIABIOCYCLO[2.2.1] HEPTANE RING SYSTEM

(75) Inventors: Dramane I. Laine, King of Prussia, PA (US); Michael R. Palovich, King of Prussia, PA (US); Brent W. McCleland, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 12/063,719

(22) PCT Filed: Aug. 17, 2006

(86) PCT No.: PCT/US2006/032138

§ 371 (c)(1),
(2), (4) Date: Feb. 13, 2008

(87) PCT Pub. No.: WO2007/022351

PCT Pub. Date: Feb. 22, 2007

(65) Prior Publication Data

US 2008/0194618 A1    Aug. 14, 2008

Related U.S. Application Data

(60) Provisional application No. 60/709,301, filed on Aug. 18, 2005.

(51) Int. Cl.
*A01N 43/42*    (2006.01)

(52) U.S. Cl. ............ 514/304; 546/112; 546/124; 548/452

(58) Field of Classification Search .......... 514/304; 546/124, 112; 548/452
See application file for complete search history.

(56) References Cited

U.S. PATENT DOCUMENTS

| | | | |
|---|---|---|---|
| 2,800,478 A | 7/1957 | Zirkle et al. | |
| 2,800,481 A | 7/1957 | Zirkle et al. | |
| 3,634,852 A | 1/1972 | Hartley et al. | |
| 5,091,397 A * | 2/1992 | Wadsworth et al. | 514/359 |
| 5,590,645 A | 1/1997 | Davies et al. | |
| 5,780,466 A | 7/1998 | Emonds-Alt et al. | |
| 5,860,419 A | 1/1999 | Davies et al. | |
| 5,873,360 A | 2/1999 | Davies et al. | |
| 6,248,752 B1 | 6/2001 | Smith | |
| 6,262,066 B1 | 7/2001 | Tulshian et al. | |
| 6,350,758 B1 | 2/2002 | Kozikowski et al. | |
| 6,455,527 B2 | 9/2002 | Tulshian et al. | |
| 6,696,462 B2 | 2/2004 | Eickmeier et al. | |
| 6,750,226 B2 | 6/2004 | Forner et al. | |
| 7,232,841 B2 | 6/2007 | Busch-Petersen et al. | |
| 7,276,521 B2 | 10/2007 | Busch-Petersen et al. | |
| 7,488,827 B2 * | 2/2009 | Laine et al. | 546/133 |
| 7,498,440 B2 * | 3/2009 | Laine et al. | 546/133 |
| 2005/0020660 A1 | 1/2005 | Guyaux et al. | |
| 2005/0113417 A1 | 5/2005 | Mammen et al. | |
| 2005/0209272 A1 | 9/2005 | Fernandez et al. | |
| 2005/0277676 A1 | 12/2005 | Laine et al. | |
| 2006/0160844 A1 | 7/2006 | Belmonte et al. | |
| 2006/0178396 A1 | 8/2006 | Belmonte et al. | |
| 2007/0129396 A1 | 6/2007 | Wan et al. | |
| 2007/0135478 A1 | 6/2007 | Palovich et al. | |
| 2007/0149598 A1 | 6/2007 | Busch-Petersen et al. | |
| 2007/0173646 A1 | 7/2007 | Laine et al. | |
| 2007/0179180 A1 | 8/2007 | Busch-Petersen et al. | |
| 2007/0179184 A1 | 8/2007 | Busch-Petersen et al. | |
| 2007/0185088 A1 | 8/2007 | Busch-Petersen et al. | |
| 2007/0185090 A1 | 8/2007 | Busch-Petersen et al. | |
| 2007/0185148 A1 | 8/2007 | Busch-Petersen et al. | |
| 2007/0185155 A1 | 8/2007 | Laine et al. | |
| 2007/0232599 A1 | 10/2007 | Palovich et al. | |
| 2007/0249664 A1 | 10/2007 | Laine et al. | |

FOREIGN PATENT DOCUMENTS

| | | |
|---|---|---|
| EP | 0069715 | 6/1982 |
| GB | 2064336 | 6/1981 |
| GB | 2129691 | 5/1984 |
| GB | 2169265 | 7/1986 |
| GB | 2178965 | 2/1987 |
| GB | 2242134 | 9/1991 |
| WO | 87/05213 | 9/1987 |
| WO | WO2005/104745 | * 11/2005 |
| WO | WO2005/112644 | * 12/2005 |
| WO | 2006/055503 | 5/2006 |
| WO | 2006/055553 | 5/2006 |
| WO | 2006/062883 | 6/2006 |
| WO | 2006/062931 | 6/2006 |

(Continued)

OTHER PUBLICATIONS

U.S. Appl. No. 10/585,830, filed Jul. 12, 2006, Laine et al.

(Continued)

*Primary Examiner*—Kamal A Saeed
*Assistant Examiner*—Valerie Rodriguez-Garcia
(74) *Attorney, Agent, or Firm*—Dara L. Dinner; Theodore R. Furman

(57) ABSTRACT

Muscarinic Acetylcholine receptor antagonists and methods of using them are provided.

26 Claims, No Drawings

FOREIGN PATENT DOCUMENTS

| WO | 2006/065755 | 6/2006 |
|----|-------------|--------|
| WO | 2006/065788 | 6/2006 |
| WO | 2007/018508 | 2/2007 |
| WO | 2007/018514 | 2/2007 |

OTHER PUBLICATIONS

U.S. Appl. No. 10/598,743, filed Sep. 11, 2006, Budzik et al.
U.S. Appl. No. 10/598,750, filed Sep. 11, 2006, Jin et al.
U.S. Appl. No. 10/599,717, filed Oct. 6, 2006, Laine et al.
U.S. Appl. No. 11/570,981, filed Dec. 20, 2006, Cooper et al.
U.S. Appl. No. 11/573,097, filed Feb. 2, 2007, Busch-Petersen et al.
U.S. Appl. No. 11/573,099, filed Feb. 2, 2007, Busch-Petersen et al.
U.S. Appl. No. 11/766,318, filed Jun. 21, 2007, Busch-Petersen et al.
U.S. Appl. No. 11/766,371, filed Jun. 21, 2007, Busch-Petersen et al.
U.S. Appl. No. 11/774,885, filed May 1, 2006, Wan et al.
U.S. Appl. No. 11/578,000, filed Apr. 26, 2007, Busch-Petersen et al.
U.S. Appl. No. 11/997,451, filed Jan. 31, 2008, Busch-Petersen et al.
U.S. Appl. No. 11/997,466, filed Jan. 31, 2008, Busch-Petersen et al.
Ran et al., *Yaoxue Xuebao*, vol. 19 (5) pp. 361-366 (1984), with translation.
Wu, et al., *Zhongguo Yaowu Huaxue Zazhi*, vol. 3(1) pp. 23-26 (1993), with translation.
Yu, et al., *Yaoxue Xuebao*, vol. 18(10) pp. 766-774 (1983), with translation.
Zhang, et al., *Yaoxue Xuebao*, vol. 20(10) pp. 752-758 (1985), with translation.
Brown, *History and Basic Properties*, Humana Press, USA pp. 7-9 (1989).
Caulfield, *Pharmac. Ther.*, vol. 58 pp. 319-379 (1993).
Costello, et al., *American Journal of Physiology*, vol. 276 (5) pp. L709-L714 (1999).
Fryer and Jacoby, *Am J Respir Crit Care Med*, vol. 158 (5, pt 3) pp. 154-160 (1998).
Fryer et al., *Life Sci*, vol. 64 (6-7) pp. 449-455 (1999).
Hedge, et al., *Life Sciences*, vol. 64 (6/7) pp. 419-428 (1999).
Ikeda, et al., *Naunyn-Schmiedeberg's Arch Pharmacol.*, vol. 366, pp. 97-103, (2002).
Minette, et al., *Journal of Applied Physiology*, vol. 67(6) pp. 2461-2465 (1989).
Oprins, et al., *Annals of the New York Academy of Sciences*, vol. 915 pp. 102-106 (2000).
Pauwels et al., *Am. J. Respir. Crit. Care Med.*, vol. 163 pp.1256-1276 (2001).
Ran, et al., *Yaoxue Xuebao*, vol. 19 (5) pp. 361-366 (1984) Abstract only.
Sarau, *Mol. Pharmacol.*, vol. 56 (3) pp. 657-663 (1999).
Van Rossum, et al., *Arch. Int. Pharmacodyn.*, vol. 143 p. 299 (1963) Best Available Copy.
Wu, et al., *Zhongguo Yaowu Huazue Zazhi*, vol. 3 (1) pp. 23-26 (1993)Abstract only.
Zirkle, et al., *J Med Chem*, vol. 27 pp. 1269-1279 (1962).
Zirkle, et al., *J Med Chem*, vol. 27 pp. 1279-1285 (1962).
Zirkle, et al., *J Med Chem*, vol. 5 pp. 341-356 (1962).
Zhang, et al., *J Med Chem*, vol. 44 pp. 3937-3945 (2001).

* cited by examiner

MUSCARINIC ACETYLCHOLINE RECEPTOR ANTAGONISTS CONTAINING AN AZONIABICYCLO[2.2.1] HEPTANE RING SYSTEM

This application is the §371 national stage entry of PCT application PCT/US06/32138 filed 17 Aug. 2006, which claims the benefit of U.S. Provisional Application No. 60/709,301, filed 18 Aug. 2005.

FIELD OF THE INVENTION

This invention relates to novel azoniabicyclo[2.2.1]heptane derivatives, pharmaceutical compositions, and use thereof in treating muscarinic acetylcholine receptor mediated diseases of the respiratory tract.

BACKGROUND OF THE INVENTION

Acetylcholine released from cholinergic neurons in the peripheral and central nervous systems affects many different biological processes through interaction with two major classes of acetylcholine receptors—the nicotinic and the muscarinic acetylcholine receptors. Muscarinic acetylcholine receptors (mAChRs) belong to the superfamily of G-protein coupled receptors that have seven transmembrane domains. There are five subtypes of mAChRs, termed $M_1$-$M_5$, and each is the product of a distinct gene. Each of these five subtypes displays unique pharmacological properties. Muscarinic acetylcholine receptors are widely distributed in vertebrate organs where they mediate many of the vital functions. Muscarinic receptors can mediate both inhibitory and excitatory actions. For example, in smooth muscle found in the airways, $M_3$ mAChRs mediate contractile responses. For review, please see Caulfield (1993 *Pharmac. Ther.* 58:319-79).

In the lungs, mAChRs have been localized to smooth muscle in the trachea and bronchi, the submucosal glands, and the parasympathetic ganglia. Muscarinic receptor density is greatest in parasympathetic ganglia and then decreases in density from the submucosal glands to tracheal and then bronchial smooth muscle. Muscarinic receptors are nearly absent from the alveoli. For review of mAChR expression and function in the lungs, please see Fryer and Jacoby (1998 *Am J Respir Crit Care Med* 158(5, pt 3) S154-60).

Three subtypes of mAChRs have been identified as important in the lungs, $M_1$, $M_2$ and $M_3$ mAChRs. The $M_3$ mAChRs, located on airway smooth muscle, mediate muscle contraction. Stimulation of $M_3$ mAChRs activates the enzyme phospholipase C via binding of the stimulatory G protein Gq/11 (Gs), leading to liberation of phosphatidyl inositol-4,5-bisphosphate, resulting in phosphorylation of contractile proteins. $M_3$ mAChRs are also found on pulmonary submucosal glands. Stimulation of this population of $M_3$ mAChRs results in mucus secretion.

$M_2$ mAChRs make up approximately 50-80% of the cholinergic receptor population on airway smooth muscles. Although the precise function is still unknown, they inhibit catecholaminergic relaxation of airway smooth muscle via inhibition of cAMP generation. Neuronal $M_2$ mAChRs are located on postganglionic parasympathetic nerves. Under normal physiologic conditions, neuronal $M_2$ mAChRs provide tight control of acetylcholine release from parasympathetic nerves. Inhibitory $M_2$ mAChRs have also been demonstrated on sympathetic nerves in the lungs of some species. These receptors inhibit release of noradrenaline, thus decreasing sympathetic input to the lungs.

$M_1$ mAChRs are found in the pulmonary parasympathetic ganglia where they function to enhance neurotransmission. These receptors have also been localized to the peripheral lung parenchyma, however their function in the parenchyma is unknown.

Muscarinic acetylcholine receptor dysfunction in the lungs has been noted in a variety of different pathophysiological states. In particular, in asthma and chronic obstructive pulmonary disease (COPD), inflammatory conditions lead to loss of inhibitory $M_2$ muscarinic acetylcholine autoreceptor function on parasympathetic nerves supplying the pulmonary smooth muscle, causing increased acetylcholine release following vagal nerve stimulation (Fryer et al. 1999 *Life Sci* 64 (6-7) 449-55). This mAChR dysfunction results in airway hyperreactivity and hyperresponsiveness mediated by increased stimulation of $M_3$ mAChRs. Thus the identification of potent mAChR antagonists would be useful as therapeutics in these mAChR-mediated disease states.

COPD is an imprecise term that encompasses a variety of progressive health problems including chronic bronchitis, chronic bronchiolitis and emphysema, and it is a major cause of mortality and morbidity in the world. Smoking is the major risk factor for the development of COPD; nearly 50 million people in the U.S. alone smoke cigarettes, and an estimated 3,000 people take up the habit daily. As a result, COPD is expected to rank among the top five as a world-wide health burden by the year 2020. Inhaled anti-cholinergic therapy is currently considered the "gold standard" as first line therapy for COPD (Pauwels et al. 2001 *Am. J. Respir. Crit. Care Med.* 163:1256-1276).

Despite the large body of evidence supporting the use of anti-cholinergic therapy for the treatment of airway hyperreactive diseases, relatively few anti-cholinergic compounds are available for use in the clinic for pulmonary indications. More specifically, in United States, Ipratropium Bromide (Atrovent©; and Combivent©, in combination with albuterol) is currently the only inhaled anti-cholinergic marketed for the treatment of airway hyperreactive diseases. While this compound is a potent anti-muscarinic agent, it is short acting, and thus must be administered as many as four times daily in order to provide relief for the COPD patient. In Europe and Asia, the long-acting anti-cholinergic Tiotropium Bromide (Spiriva©) was recently approved, however this product is currently not available in the United States. Thus, there remains a need for novel compounds that are capable of causing blockade at mAChRs which are long acting and can be administered once-daily for the treatment of airway hyperreactive diseases such as asthma and COPD.

Since mAChRs are widely distributed throughout the body, the ability to apply anti-cholinergics locally and/or topically to the respiratory tract is particularly advantageous, as it would allow for lower doses of the drug to be utilized. Furthermore, the ability to design topically active drugs that have long duration of action, and in particular, are retained either at the receptor or by the lung, would allow the avoidance of unwanted side effects that may be seen with systemic anticholinergic use.

SUMMARY OF THE INVENTION

This invention provides for a method of treating a muscarinic acetylcholine receptor (mAChR) mediated disease, wherein acetylcholine binds to an mAChR and which method comprises administering an effective amount of a compound of Formula (I) or a pharmaceutically acceptable salt thereof.

This invention also relates to a method of inhibiting the binding of acetylcholine to its receptors in a mammal in need thereof which comprises administering to aforementioned mammal an effective amount of a compound of Formula (I).

The present invention also provides for the novel compounds of Formula (I), and pharmaceutical compositions comprising a compound of Formula (I), and a pharmaceutical carrier or diluent.

Compounds of Formula (I) useful in the present invention are represented by the structure:

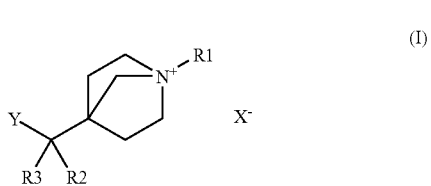
(I)

wherein:
Y is OH or CN;
R1 is selected from the group consisting of C1-15 alkyl, cyanosubstituted C1-15 alkyl, halosubstituted C1-15 alkyl, C1-15 alkyl cycloalkyl, C2-15 alkenyl, hydroxy substituted C1-15 alkyl, C2-15 alkyl aryl, C2-15 alkyl heteroaryl, (CR7R7)qOC(O)Ra, and (CR7R7)qORc; or
R1 is:

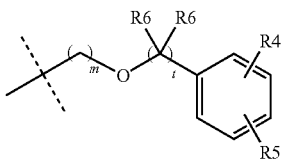

wherein:
R4 and R5 are, independently, selected from the group consisting of hydrogen, halogen, C1-4 alkyl, aryl, C1-4 alkyl aryl, cyano, nitro, (CR7R7)pORb, or R4 and R5 together may form a 5 to 6 membered saturated or unsaturated ring; and wherein the alkyl, aryl, arylalkyl, heteroaryl, heteroalkyl, heterocyclic, heterocyclicalkyl groups may be optionally substituted;
R6 is selected from the group consisting of hydrogen, and C1-4 alkyl;
m is an integer having a value of 1 to 15;
R2 and R3 are, independently, selected from the group consisting of aryl and heteroaryl, all of which moieties may be optionally substituted;
Ra is selected from the group consisting of hydrogen, C1-15 alkyl, C1-15 alkoxy and aryl, all of which moieties may be optionally substituted;
Rc is selected from the group consisting of hydrogen, C1-15 alkyl, C1-15 alkoxy, heterocyclic and a C1-15 alkyl heterocyclic moiety, all of which moieties may be optionally substituted;
t is 0 or an integer having a value of 1 to 5;
p is 0 or an integer having a value of 1 to 4;
q is an integer having a value of 1 to 5;
Rb is hydrogen, or C1-4 alkyl; and
X— is a physiologically acceptable anion, such as chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

DETAILED DESCRIPTION OF THE INVENTION

This invention related to novel azoniabicyclo[2.2.1]heptane compounds, pharmaceutical compositions, processes for their preparation, and use thereof in treating mAChR mediated diseases.

In a preferred embodiment of the present invention the compound is of formula (I) herein below:

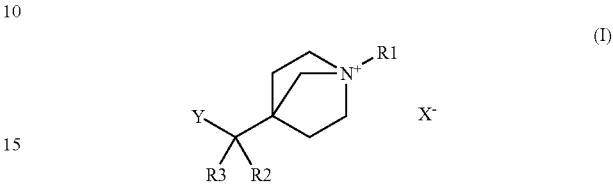
(I)

wherein:
Y is OH or CN;
R1 is selected from the group consisting of C7-12 alkyl and (CR7R7)qOC(O)Ra;
or R1 is:

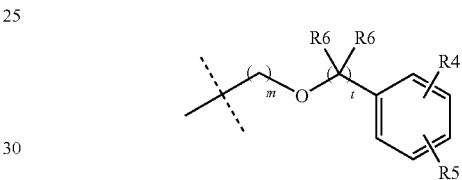

wherein:
R4 and R5 are, independently, selected from the group consisting of hydrogen, halogen, hydroxyl, methoxy, cyano, nitro, or R4 and R5 together may form 6 membered saturated ring;
R6 is hydrogen;
m is an integer having a value of 1 to 5;
R2 and R3 are, independently, selected from the group consisting of aryl and heteroaryl, all of which moieties may be optionally substituted;
Ra is aryl, which may be optionally substituted;
t is 0 or an integer having a value of 1 to 5;
q is an integer having a value of 1 to 5; and
X— is a physiologically acceptable anion, such as chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

All of the aryl, heteroaryl, and heterocyclic containing moieties may be optionally substituted as defined herein below.

For use herein the term "the aryl, heteroaryl, and heterocyclic containing moieties" refers to both the ring and the alkyl, or if included, the alkenyl rings, such as aryl, arylalkyl, and aryl alkenyl rings. The term "moieties" and "rings" may be interchangeably used throughout.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; $S(O)_{m'}$ $C_{1-10}$ alkyl, wherein m' is 0, 1 or 2, such as methyl thio, methyl sulfinyl or methyl sulfonyl; amino, mono & di-substituted amino, such as in the $NR_{10}R_{11}$ group; $NHC(O)R_9$; $C(O)NR_{10}R_{11}$; $C(O)OH$; $S(O)_2NR_{10}R_{11}$; $NHS(O)_2R_9$, $C_{1-10}$ alkyl, such as methyl, ethyl, propyl, isopropyl, or t-butyl; halosubstituted $C_{1-10}$ alkyl, such $CF_3$; an optionally substituted aryl, such as phenyl, or an optionally substituted arylalkyl, such as benzyl or phenethyl, optionally substituted heterocylic, optionally substituted heterocyclicalkyl, optionally substituted heteroaryl, optionally substituted heteroaryl alkyl, wherein these aryl, heteroaryl, or heterocyclic moieties may be substituted one to two times by halogen; hydroxy; hydroxy substituted alkyl; $C_{1-10}$ alkoxy; $S(O)_m C_{1-10}$ alkyl; amino, mono & di-substituted alkyl amino, such as in the $NR_{10}R_{11}$ group; $C_{1-10}$ alkyl, or halosubstituted $C_{1-10}$ alkyl, such as $CF_3$.

The following terms, as used herein, refer to:
"halo"—all halogens, that is chloro, fluoro, bromo and iodo.
"$C_{1-10}$alkyl" or "alkyl"—both straight and branched chain moieties of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.
"cycloalkyl" is used herein to mean cyclic moiety, preferably of 3 to 8 carbons, including but not limited to cyclopropyl, cyclopentyl, cyclohexyl, and the like.
"alkenyl" is used herein at all occurrences to mean straight or branched chain moiety of 2-10 carbon atoms, unless the chain length is limited thereto, including, but not limited to ethenyl, 1-propenyl, 2-propenyl, 2-methyl-1-propenyl, 1-butenyl, 2-butenyl and the like.
"aryl"-phenyl and naphthyl;
"heteroaryl" (on its own or in any combination, such as "heteroaryloxy", or "heteroaryl alkyl")—a 5-10 membered aromatic ring system in which one or more rings contain one or more heteroatoms selected from the group consisting of N, O or S, such as, but not limited to, pyrrole, pyrazole, furan, thiophene, quinoline, isoquinoline, quinazolinyl, pyridine, pyrimidine, oxazole, tetrazole, thiazole, thiadiazole, triazole, imidazole, indole or benzimidazole.
"heterocyclic" (on its own or in any combination, such as "heterocyclicalkyl")—a saturated or partially unsaturated 4-10 membered ring system in which one or more rings contain one or more heteroatoms selected from the group consisting of N, O, or S; such as, but not limited to, pyrrolidine, piperidine, piperazine, morpholine, tetrahydropyran, thiomorpholine, or imidazolidine. Furthermore, sulfur may be optionally oxidized to the sulfone or the sulfoxide.
"arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.
"sulfinyl"—the oxide S(O) of the corresponding sulfide, the term "thio" refers to the sulfide, and the term "sulfonyl" refers to the fully oxidized $S(O)_2$ moiety.
"wherein two $R_1$ moieties (or two Y moieties) may together form a 5 or 6 membered saturated or unsaturated ring" is used herein to mean the formation of an aromatic ring system, such as naphthalene, or is a phenyl moiety having attached a 6 membered partially saturated or unsaturated ring such as a $C_6$ cycloalkenyl, i.e. hexene, or a $C_5$ cycloalkenyl moiety, such as cyclopentene.

Illustrative examples of this invention include
4-[hydroxy(diphenyl)methyl]-1-{2-[(phenylmethyl)oxy]ethyl}-1-azoniabicyclo[2.2.1]heptane bromide
4-[hydroxy(diphenyl)methyl]-1-(2-phenylethyl)-1-azoniabicyclo[2.2.1]heptane bromide
1-ethyl-4-[hydroxy(diphenyl)methyl]-1-azoniabicyclo[2.2.1]heptane bromide
4-[hydroxy(diphenyl)methyl]-1-nonyl-1-azoniabicyclo[2.2.1]heptane bromide
4-[hydroxy(diphenyl)methyl]-1-[2-(methyloxy)ethyl]-1-azoniabicyclo[2.2.1]heptane bromide
4-[hydroxy(diphenyl)methyl]-1-[4-(phenyloxy)butyl]-1-azoniabicyclo[2.2.1]heptane bromide
4-[hydroxy(diphenyl)methyl]-1-{3-[(phenylmethyl)oxy]propyl}-1-azoniabicyclo[2.2.1]heptane bromide
4-[hydroxy(diphenyl)methyl]-1-({4-[(trifluoromethyl)oxy]phenyl}methyl)-1-azoniabicyclo[2.2.1]heptane bromide
4-[hydroxy(diphenyl)methyl]-1-[2-(phenyloxy)ethyl]-1-azoniabicyclo[2.2.1]heptane bromide
1-hexyl-4-[hydroxy(diphenyl)methyl]-1-azoniabicyclo[2.2.1]heptane bromide
4-[hydroxy(diphenyl)methyl]-1-{4-[(phenylmethyl)oxy]butyl}-1-azoniabicyclo[2.2.1]heptane bromide
1-(cyclohexylmethyl)-4-[hydroxy(diphenyl)methyl]-1-azoniabicyclo[2.2.1]heptane bromide
4-[hydroxy(diphenyl)methyl]-1-[2-({[3-(methyloxy)phenyl]methyl}oxy)ethyl]-1-azoniabicyclo[2.2.1]heptane bromide
1-{3-[(4-bromophenyl)oxy]propyl}-4-[hydroxy(diphenyl)methyl]-1-azoniabicyclo[2.2.1]heptane bromide
4-[hydroxy(diphenyl)methyl]-1-{2-[(phenylcarbonyl)oxy]ethyl}-1-azoniabicyclo[2.2.1]heptane bromide
4-[hydroxy(diphenyl)methyl]-1-{3-[(4-nitrophenyl)oxy]propyl}-1-azoniabicyclo[2.2.1]heptane bromide
4-[hydroxy(diphenyl)methyl]-1-{3-[(2-hydroxyphenyl)oxy]propyl}-1-azoniabicyclo[2.2.1]heptane bromide
4-[hydroxy(diphenyl)methyl]-1-[3-(2-naphthalenyloxy)propyl]-1-azoniabicyclo[2.2.1]heptane bromide
1-{3-[(3-chlorophenyl)oxy]propyl}-4-[hydroxy(diphenyl)methyl]-1-azoniabicyclo[2.2.1]heptane bromide
4-[hydroxy(diphenyl)methyl]-1-{[3-(methyloxy)phenyl]methyl}-1-azoniabicyclo[2.2.1]heptane bromide
1-(5-hexen-1-yl)-4-[hydroxy(diphenyl)methyl]-1-azoniabicyclo[2.2.1]heptane bromide
4-[hydroxy(diphenyl)methyl]-1-(6-hydroxyhexyl)-1-azoniabicyclo[2.2.1]heptane bromide
4-[hydroxy(diphenyl)methyl]-1-[3-(phenyloxy)propyl]-1-azoniabicyclo[2.2.1]heptane bromide
4-[cyano(diphenyl)methyl]-1-(phenylmethyl)-1-azoniabicyclo[2.2.1]heptane bromide
4-[cyano(diphenyl)methyl]-1-{2-[(phenylmethyl)oxy]ethyl}-1-azoniabicyclo[2.2.1]heptane bromide
4-[cyano(diphenyl)methyl]-1-ethyl-1-azoniabicyclo[2.2.1]heptane bromide
4-[cyano(diphenyl)methyl]-1-[3-(methyloxy)propyl]-1-azoniabicyclo[2.2.1]heptane bromide
4-[cyano(diphenyl)methyl]-1-(3-phenylpropyl)-1-azoniabicyclo[2.2.1]heptane bromide
4-[cyano(diphenyl)methyl]-1-hexyl-1-azoniabicyclo[2.2.1]heptane bromide
4-[cyano(diphenyl)methyl]-1-(2-hydroxyethyl)-1-azoniabicyclo[2.2.1]heptane bromide
4-[cyano(diphenyl)methyl]-1-(cyclohexylmethyl)-1-azoniabicyclo[2.2.1]heptane bromide
4-[cyano(diphenyl)methyl]-1-[2-(1H-indol-2-yl)ethyl]-1-azoniabicyclo[2.2.1]heptane bromide
4-[cyano(diphenyl)methyl]-1-(3-cyanopropyl)-1-azoniabicyclo[2.2.1]heptane bromide 4-[cyano(diphenyl)methyl]-1-[3-(phenyloxy)propyl]-1-azoniabicyclo[2.2.1]heptane bromide Methods of Preparation The compounds of Formula (I) may be obtained by applying synthetic procedures, some of which are illustrated in the Scheme below. The synthesis provided in this Scheme is applicable for producing compounds of Formula (I) having a variety of different R1, R2 and R3 groups which are reacted, employing substituents which are suitably protected, to achieve compatibility with the reactions outlined herein. Subsequent deprotection, in those cases, then affords compounds of the nature generally disclosed. While the Schemes are shown with compounds only of Formula (I), this is merely for illustration purpose only.

As shown in Scheme 1, the desired compounds of Formula (I) can be prepared in either 2 (for the alcohol) or 3 (for the CN) synthetic steps from ethyl i-azabicyclo[2.2.1]heptane-4-carboxylate 1 (as prepared in *Tetrahedron Letters,* 1991, pp 1245-46). Condensation of ester 1 with organometallic reagents such as a Grignard reagent or an organolithium derivative in an aprotic solvent such as tetrahydrofuran, resulted in the formation of the tertiary alcohol 2 of Formula (I) (R1=nothing). Cyanation of compound 2 with TMSCN and AlCl₃ resulted in the cyano compound 3 of Formula (I) (R1=nothing). Further N-alkylation of compounds 2 and 3 with a suitable alkyl halide in an organic solvent such as chloroform or acetonitrile gives compounds 4 and 5 respectively of Formula (I).

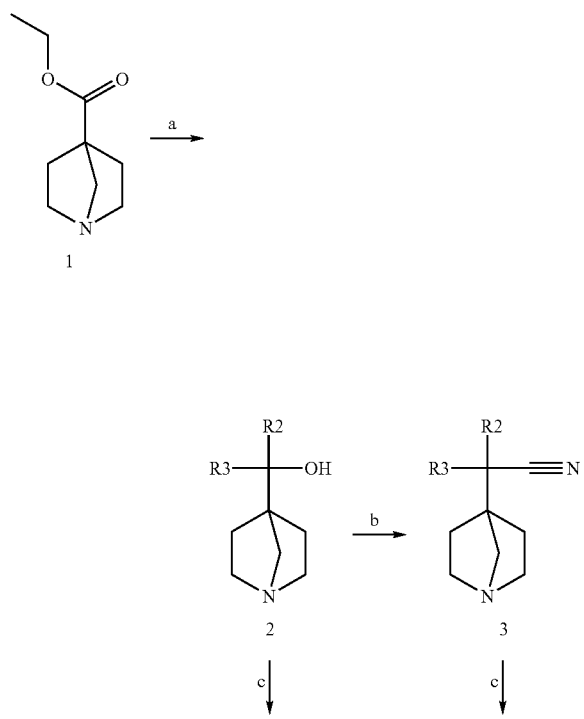

Scheme 1

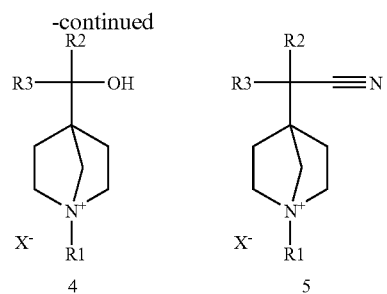

Reagents and conditions:
a   R₂M then R₃M, THF;
b   AlCl₃, TMSCN, DCE, 85° C.;
c   R1X, ACN, CHCl₃, 60° C.

SYNTHETIC EXAMPLES

The invention will now be described by reference to the following Examples which are merely illustrative and are not to be construed as a limitation of the scope of the present invention. All temperatures are given in ° C. Thin layer chromatography (t.l.c.) was carried out on silica, and column chromatography on silica (Flash column chromatography using Merck 9385 unless stated otherwise).

The following are the experimental conditions for the LC-MS.

LC-MS Experimental Conditions:

Liquid Chromatograph:

System: Shimadzu LC system with SCL-10A Controller and dual UV detector

| Autosampler: | Leap CTC with a Valco six port injector |
| --- | --- |
| Column: | Aquasil/Aquasil (C18 40 × 1 mm) |
| Inj. Volume (µL): | 2.0 |
| Solvent A: | H2O, 0.02% TFA |
| Solvent B: | MeCN, 0.018% TFA |
| Gradient: | linear |
| Channel A: | UV 214 nm |
| Channel B: | ELS |

| Step | Time (min) | Dura. (min) | Flow (µL/min) | Sol. A | Sol. B |
| --- | --- | --- | --- | --- | --- |
| 0 | 0.00 | 0.00 | 300.00 | 95.00 | 5.00 |
| 1 | 0.00 | 0.01 | 300.00 | 95.00 | 5.00 |
| 2 | 0.01 | 3.20 | 300.00 | 10.00 | 90.00 |
| 3 | 3.21 | 1.00 | 300.00 | 10.00 | 90.00 |
| 4 | 4.21 | 0.10 | 300.00 | 95.00 | 5.00 |
| 5 | 4.31 | 0.40 | 300.00 | 95.00 | 5.00 |

| Mass Spectrometer: | PE Sciex Single Quadrupole LC/MS API-150 |
| --- | --- |
| Polarity: | Positive |
| Acquisition mode: | Profile |

The Gilson preparatory HPLC was conducted under the following conditions:
Column: 75×33 mm I.D., S-5 um, 12 nm
Flow rate: 30 mL/min
Injection Volume: 0.800 mL
Room temperature
Solvent A: water
Solvent B: acetonitrile All solvents used herein are of the highest available purity and all reactions are run under anhydrous conditions under an air atmosphere unless otherwise indicated.

Example 1

Preparation of 4-[hydroxy(diphenyl)methyl]-1-{2-[(phenylmethyl)oxy]ethyl}-1-azoniabicyclo[2.2.1]heptane bromide 1-Azabicyclo[2.2.1]hept-4-yl(diphenyl)methanol A solution of ethyl 1-azabicyclo[2.2.1]heptane-4-carboxylate (4 g, 23 mmol) in THF (60 mL) was added dropwise to a solution of phenyllithium (1.5 M in 70% cyclohexane/30% diethyl ether, 63.1 mL, 94.6 mmol) pre-cooled to −30° C. under Ar. The reaction was warmed to RT and stirred for 16 h. The reaction was treated with water and extracted with ethyl acetate. The combined extracts were washed with brine, dried (MgSO$_4$), filtered and concentrated in vacuo. Trituration (diethyl ether) afforded the title compound (3.595 g, 54%). EI-MS m/z 280 (MH)$^+$ Rt (1.56 min).

4-[Hydroxy(diphenyl)methyl]-1-{2-[(phenylmethyl)oxy]ethyl}-1-azoniabicyclo[2.2.1]heptane bromide General Procedure for Salt Formation with HPLC Purification To a solution of 1-azabicyclo[2.2.1]hept-4-yl(diphenyl)methanol (50 mg, 0.18 mmol) in 2 CH$_3$CN/3 CHCl$_3$ (4 mL) was added 2-bromoethyl phenylmethyl ether (0.04 mL, 0.25 mmol). The solution was heated at 60° C. for 16 h, cooled down to room temperature and the solvents evaporated under vacuum. The residue was taken up in 2.5 mL of DMSO and purified by preparatory HPLC (without TFA) to give the title compound (32 mg, 36%). EI-MS m/z 414 (M$^+$) Rt (1.92 min).

Example 2

Preparation of 4-[hydroxy(diphenyl)methyl]-1-(2-phenylethyl)-1-azoniabicyclo[2.2.1]heptane bromide General Procedure for Salt Formation without HPLC Purification.

To a solution of 1-azabicyclo[2.2.1]hept-4-yl(diphenyl)methanol (30.5 mg, 0.109 mmol) in 2 CH$_3$CN/3 CHCl$_3$ (2.5 mL) was added (2-bromoethyl)benzene (0.03 mL, 0.22 mmol). The solution was stirred at 60° C. for 16 h. The reaction was cooled down to room temperature. Trituration with ethyl acetate caused a solid to crash out of solution. This solid was filtered off, and washed with ethyl acetate to give the title compound (36.4 mg, 72%). EI-MS m/z 384 (M$^+$) Rt (1.87 min).

Example 3

Preparation of 1-ethyl-4-[hydroxy(diphenyl)methyl]-1-azoniabicyclo[2.2.1]heptane bromide Following the general procedure outlined in Example 2, 1-azabicyclo[2.2.1]hept-4-yl(diphenyl)methanol (31.3 mg, 0.112 mmol) and bromoethane (0.03 mL, 0.4 mmol) in 2 CH$_3$CN/3 CHCl$_3$ (2.5 mL) were reacted to give the desired product (28.4 mg, 65%). EI-MS m/z 308 (M$^+$) Rt (1.49 min).

Example 4

Preparation of 4-[hydroxy(diphenyl)methyl]-1-nonyl-1-azoniabicyclo[2.2.1]heptane bromide Following the general procedure outlined in Example 2, 1-azabicyclo[2.2.1]hept-4-yl(diphenyl)methanol (29.3 mg, 0.105 mmol) and 1-bromononane (0.04 mL, 0.2 mmol) in 2 CH$_3$CN/3 CHCl$_3$ (2.5 mL) were reacted to give the desired product (31.5 mg, 62%). EI-MS m/z 407 (M$^+$) Rt (2.23 min).

Example 5

Preparation of 4-[hydroxy(diphenyl)methyl]-1-[2-(methyloxy)ethyl]-1-azoniabicyclo[2.2.1]heptane bromide Following the general procedure outlined in Example 1, 1-azabicyclo[2.2.1]hept-4-yl(diphenyl)methanol (30.8 mg, 0.110 mmol) and 1-bromo-2-(methyloxy)ethane (0.03 mL, 0.3 mmol) in 2 CH$_3$CN/3 CHCl$_3$ (2.5 nm) were reacted to give the desired product (11.1 mg, 24%). EI-MS m/z 338 (M$^+$) Rt (1.64 min).

Example 6

Preparation of 4-[hydroxy(diphenyl)methyl]-1-[4-(phenyloxy)butyl]-1-azoniabicyclo[2.2.1]heptane bromide Following the general procedure outlined in Example 2, 1-azabicyclo[2.2.1]hept-4-yl(diphenyl)methanol (31.8 mg, 0.114 mmol) and 4-bromobutyl phenyl ether (44.3 mg, 0.193 mmol) in 2 CH$_3$CN/3 CHCl$_3$ (2.5 mL) were reacted to give the desired product (38.7 mg, 67%). EI-MS m/z 428 (M$^+$) Rt (1.98 min).

Example 7

Preparation of 4-[hydroxy(diphenyl)methyl]-1-{3-[(phenylmethyl)oxy]propyl}-1-azoniabicyclo[2.2.1]heptane bromide Following the general procedure outlined in Example 2, 1-azabicyclo[2.2.1]hept-4-yl(diphenyl)methanol (30.4 mg, 0.109 mmol) and 3-bromopropyl phenylmethyl ether (0.03 mL, 0.17 mmol) in 2 CH$_3$CN/3 CHCl$_3$ (2.5 mL) were reacted to give the desired product (29.1 mg, 53%). EI-MS m/z 428 (M$^+$) Rt (1.93 min).

Example 8

Preparation of 4-[hydroxy(diphenyl)methyl]-1-({4-[(trifluoromethyl)oxy]phenyl}methyl)-1-azoniabicyclo[2.2.1]heptane bromide Following the general procedure outlined in Example 2, 1-azabicyclo[2.2.1]hept-4-yl(diphenyl)methanol (29.9 mg, 0.107 mmol) and 4-(bromomethyl)phenyl trifluoromethyl ether (51 mg, 0.20 mmol) in 2 CH$_3$CN/3 CHCl$_3$ (2.5 mL) were reacted to give the desired product (41.3 mg, 72%). EI-MS m/z 454 (M$^+$) Rt (1.95 rain).

Example 9

Preparation of 4-[hydroxy(diphenyl)methyl]-1-[2-(phenyloxy)ethyl]-1-azoniabicyclo[2.2.1]heptane bromide Following the general procedure outlined in Example 2, 1-azabicyclo[2.2.1]hept-4-yl(diphenyl)methanol (30.8 mg, 0.110 mmol) and 2-bromoethyl phenyl ether (35.7 mg, 0.177 mmol) in 2 $CH_3CN/3CHCl_3$ (2.5 mL) were reacted to give the desired product (33.1 mg, 62%). EI-MS m/z 400 ($M^+$) Rt (1.86 min).

Example 10

Preparation of 4-[hydroxy(diphenyl)methyl]-1-methyl-1-azoniabicyclo[2.2.1]heptane bromide Following the general procedure outlined in Example 2, 1-azabicyclo[2.2.1]hept-4-yl(diphenyl)methanol (30.0 mg, 0.107 mmol) and bromomethane (0.09 mL, 0.18 mmol) in 2 $CH_3CN/3\ CHCl_3$ (2.5 mL) were reacted to give the desired product (26.3 mg, 65%). EI-MS m/z 294 ($M^+$) Rt (1.30 min).

Example 11

Preparation of 4-[hydroxy(diphenyl)methyl]-1-{4-[(phenylmethyl)oxy]butyl}-1-azoniabicyclo[2.2.1]heptane bromide Following the general procedure outlined in Example 1, 1-azabicyclo[2.2.1]hept-4-yl(diphenyl)methanol (33.1 mg, 0.118 mmol) and 4-bromobutyl phenylmethyl ether (0.04 mL, 0.21 mmol) in 2 $CH_3CN/3\ CHCl_3$ (2.5 mL) were reacted to give the desired product (4.5 mg, 7%). EI-MS m/z 442 ($M^+$) Rt (2.01 min).

Example 12

Preparation of 1-(cyclohexylmethyl)-4-[hydroxy(diphenyl)methyl]-1-azoniabicyclo[2.2.1]heptane bromide Following the general procedure outlined in Example 1, 1-azabicyclo[2.2.1]hept-4-yl(diphenyl)methanol (33.0 mg, 0.118 mmol) and (bromomethyl)cyclohexane (0.03 mL, 0.21 mmol) in 2 $CH_3CN/3\ CHCl_3$ (2.5 mL) were reacted to give the desired product (7 mg, 13%). EI-MS m/z 376 ($M^+$) Rt (1.90 min).

Example 13

Preparation of 4-[hydroxy(diphenyl)methyl]-1-[2-({[3-(methyloxy)phenyl]methyl}oxy)ethyl]-1-azoniabicyclo[2.2.1]heptane bromide

2-({[3-(Methyloxy)phenyl]methyl}oxy)ethanol

Ethylene glycol (0.084 mL, 1.51 mmol) was added to NaH (38 mg, 1.5 mmol, 95% in oil) in THF (3 mL). 3-(Chloromethyl)phenyl methyl ether (0.21 mL, 1.5 mmol) was added to the reaction, and the residual 3-(Chloromethyl)phenyl methyl ether was transferred to the reaction tube with additional THF (1 mL). $(Bu)_4NI$ (55 mg, 0.15 mmol) was then added, and the reaction was heated at 60° C. for 18 h and then rt for 4 h. $H_2O$ (2 mL) and EtOAc (2 mL) were added, and the layers were separated via pipette. The aqueous layer was extracted with EtOAc (1×1 mL), and the combined organic layers were concentrated. The crude product was purified by flash chromatography eluting with 30% EtOAc/hexanes at 5 mL/min (10 mL) to give the title compound (114 mg, 42%). The product was characterized by $^1H$ NMR (400 MHz) in $CDCl_3$.

1-{[(2-Bromoethyl)oxy]-methyl}-3-(methyloxy)benzene

A solution of N-bromosuccinimide (272 mg, 1.53 mmol) in DCM (2.5 mL) was added to resin-bound triphenylphosphine (510 mg, 1.53 mEquiv, Fluka) in DCM (2.5 mL), and the reaction was stirred at rt for 10 min. A solution of 2-({[3-(methyloxy)phenyl]methyl}oxy)ethanol (114 mg, 0.626 mmol) in DCM (1.5 mL) was added to the reaction, and the residual alcohol was transferred with additional DCM (1.5 mL). The reaction vial was capped, wrapped in aluminum foil, and stirred at rt for 20 h. The reaction was filtered through a SPE cartridge (5 g silica) eluting with the following 10 mL fractions: DCM (fraction 1), 30% EtOAc/hexanes (fraction 2), and 50% EtOAc/hexanes (fraction 3) to give the title compound (160 mg, title compound and impurity). The product was characterized by $^1H$ NMR (400 MHz) in $CDCl_3$. The purity of the compound was good enough to carry on the next reaction.

4-[Hydroxy(diphenyl)methyl]-1-[2-({[3-(methyloxy)phenyl]methyl}oxy)ethyl]-1-azoniabicyclo[2.2.1]heptane bromide Following the general procedure outlined in Example 2, 1-azabicyclo[2.2.1]hept-4-yl(diphenyl)methanol (33.0 mg, 0.118 mmol) and 1-{[(2-bromoethyl)oxy]methyl}-3-(methyloxy)benzene (42.5 mg, 0.173 mmol) in 2 $CH_3CN/3\ CHCl_3$ (2.5 mL) were reacted to give the desired product (22.8 mg, 37%). EI-MS m/z 444 ($M^+$) Rt (1.96 min).

Example 14

Preparation of 4-[hydroxy(diphenyl)methyl]-1-[3-(phenyloxy)propyl]-1-azoniabicyclo[2.2.1]heptane bromide Following the general procedure outlined in Example 2, 1-azabicyclo[2.2.1]hept-4-yl(diphenyl)methanol (31.5 mg, 0.113 mmol) and 4-bromophenyl 3-bromopropyl ether (46.1 mg, 0.157 mmol) in 2 $CH_3CN/3\ CHCl_3$ (2.5 mL) were reacted to give the desired product (35.7 mg, 55%). EI-MS m/z 492 ($M^+$) Rt (1.94 min).

Example 15

Preparation of 4-[hydroxy(diphenyl)methyl]-1-{2-[(phenylcarbonyl)oxy]ethyl}-1-azoniabicyclo[2.2.1]heptane bromide Following the general procedure outlined in Example 1, 1-azabicyclo[2.2.1]hept-4-yl(diphenyl)methanol (32.2 mg, 0.115 mmol) and methyl 4-(bromomethyl)benzoate (0.03 mL, 0.19 mmol) in 2 $CH_3CN/3\ CHCl_3$ (2.5 mL) were reacted to give the desired product (4 mg, 7%). EI-MS m/z 428 ($M^+$) Rt (1.69 min).

Example 16

Preparation of 4-[hydroxy(diphenyl)methyl]-1-{3-[(4-nitrophenyl)oxy]propyl}-1-azoniabicyclo[2.2.1]heptane bromide Following the general procedure outlined in Example 2, 1-azabicyclo[2.2.1]hept-4-yl(diphenyl)methanol (33.2 mg, 0.119 mmol) and 1-(bromomethyl)-4-nitrobenzene (45.9 mg, 0.176 mmol) in 2 $CH_3CN$/3 $CHCl_3$ (2.5 mL) were reacted to give the desired product (32.7 mg, 51%). EI-MS m/z 459 ($M^+$) Rt (1.83 min).

Example 17

Preparation of 4-[hydroxy(diphenyl)methyl]-1-{3-[(2-hydroxyphenyl)oxy]propyl}-1-azoniabicyclo[2.2.1]heptane bromide Following the general procedure outlined in Example 2, 1-azabicyclo[2.2.1]hept-4-yl(diphenyl)methanol (30.9 mg, 0.111 mmol) and 2-[(3-bromopropyl)oxy]phenol (47.9 mg, 0.207 mmol) in 2 $CH_3CN$/3 $CHCl_3$ (2.5 mL) were reacted to give the desired product (20.9 mg, 37%). EI-MS m/z 430 ($M^+$) Rt (1.70 min).

Example 18

Preparation of 4-[hydroxy(diphenyl)methyl]-1-[3-(2-naphthalenyloxy)propyl]-1-azoniabicyclo[2.2.1]heptane bromide Following the general procedure outlined in Example 2, 1-azabicyclo[2.2.1]hept-4-yl(diphenyl)methanol (31.5 mg, 0.113 mmol) and 2-[(3-bromopropyl)oxy]naphthalene (45.5 mg, 0.172 mmol) in 2 $CH_3CN$/3 $CHCl_3$ (2.5 mL) were reacted to give the desired product (47.5 mg, 77%). EI-MS m/z 464 ($M^+$) Rt (2.0 min).

Example 19

Preparation of 1-{3-[(3-chlorophenyl)oxy]propyl}-4-[hydroxy(diphenyl)methyl]-1-azoniabicyclo[2.2.1]heptane bromide Following the general procedure outlined in Example 2, 1-azabicyclo[2.2.1]hept-4-yl(diphenyl)methanol (31.9 mg, 0.114 mmol) and 3-bromopropyl 3-chlorophenyl ether (50.6 mg, 0.203 mmol) in 2 $CH_3CN$/3 $CHCl_3$ (2.5 mL) were reacted to give the desired product (28.7 mg, 48%). EI-MS m/z 448 ($M^+$) Rt (2.0 min).

Example 20

Preparation of 4-[hydroxy(diphenyl)methyl]-1-{[3-(methyloxy)phenyl]methyl}-1-azoniabicyclo[2.2.1]heptane bromide Following the general procedure outlined in Example 1, 1-azabicyclo[2.2.1]hept-4-yl(diphenyl)methanol (29.3 mg, 0.105 mmol) and 3-(bromomethyl)phenyl methyl ether (0.03 mL, 0.21 mmol) in 2 $CH_3CN$/3 $CHCl_3$ (2.5 mL) were reacted to give the desired product (5 mg, 10%). EI-MS m/z 400 ($M^+$) Rt (1.72 min).

Example 21

Preparation of 4-[hydroxy(diphenyl)methyl]-1-[2-(1H-indol-3-yl)ethyl]-1-azoniabicyclo[2.2.1]heptane bromide Following the general procedure outlined in Example 2, 1-azabicyclo[2.2.1]hept-4-yl(diphenyl)methanol (29.7 mg, 0.106 mmol) and 3-(2-bromoethyl)-1H-indole (40.5 mg, 0.181 mmol) in 2 $CH_3CN$/3 $CHCl_3$ (2.5 mL) were reacted to give the desired product (37.0 mg, 69%). EI-MS m/z 423 ($M^+$) Rt (1.82 min).

Example 22

Preparation of 4-[hydroxy(diphenyl)methyl]-1-(6-hydroxyhexyl)-1-azoniabicyclo[2.2.1]heptane bromide Following the general procedure outlined in Example 1, 1-azabicyclo[2.2.1]hept-4-yl(diphenyl)methanol (32.0 mg, 0.116 mmol) and 6-bromo-1-hexanol (0.03 mL, 0.248 mmol) in 2 $CH_3CN$/3 $CHCl_3$ (2.5 mL) were reacted to give the desired product (3 mg, 6%). EI-MS m/z 380 ($M^+$) Rt (1.64 min).

Example 23

Preparation of 4-[hydroxy(diphenyl)methyl]-1-[3-(phenyloxy)propyl]-1-azoniabicyclo[2.2.1]heptane bromide Following the general procedure outlined in Example 2, 1-azabicyclo[2.2.1]hept-4-yl(diphenyl)methanol (0.2 mg, 0.7 mmol) and 3-bromopropylphenyl-ether (0.17 mL, 1.1 mmol) in 2 $CH_3CN$/3 $CHCl_3$ (15 mL) were reacted to give the desired product (255 mg, 64%). $^1$H NMR (400 MHz, $CD_3OD$) δ 7.5 (m, 4H), 7.35 (m, 3H), 7.3-7.2 (m, 4H), 6.9 (m, 4H), 4.07 (m, 3H), 3.8-3.7 (m, 2H), 3.62 (m, 5H), 3.6-2.5 (m, 2H), 2.4-2.3 (m, 2H), 2.3-2.1 (m, 5l).

Example 24

Preparation of 4-[cyano(diphenyl)methyl]-1-(phenylmethyl)-1-azoniabicyclo[2.2.1]heptane bromide Preparation of 1-azabicyclo[2.2.1]hept-4-yl(diphenyl)acetonitrile To a suspension of 1-azabicyclo[2.2.1]hept-4-yl(diphenyl)methanol (0.906 g, 3.24 mmol) in 1,2-dichloroethane (48 mL) was added $AlCl_3$ (2.028 g, 15.3 mmol). The reaction was allowed to stir for 10 nm in and then TMSCN (2.04 mL, 15.3 mmol) was added. The reaction was sealed and heated to 85° C. for overnight. The reaction mixture was poured into a separatory funnel containing $K_2CO_3$ (aq satd) (200 mL) and EtOAc (200 mL). Extraction with EtOAc (3×200 mL) was performed. The combined organics were dried over $MgSO_4$, filtered and concentrated under vacuum. The residue was dissolved in DMSO and purified by Gilson preparatory HPLC (w/0.1% TFA). The combined fractions were concentrated down under vacuum to remove the $CH_3CN$. The resulting water layer was basified to pH=12 with 5N NaOH, and then extracted with EtOAc (3×150 mL). The combined fractions were dried over $MgSO_4$, filtered, and concentrated under vacuum to give the title compound (0.53 g, 56.7%). EI-MS m/z 289 (M-H)+Rt (1.43 min).

General Procedure for Salt Formation with HPLC Purification.

To a solution of 1-azabicyclo[2.2.1]hept-4-yl(diphenyl)acetonitrile (0.044 g, 0.152 mmol) in 2CH$_3$CN/3CHCl$_3$ (3.5 mL) was added (bromomethyl)benzene (0.030 mL, 0.252 mmol). The solution was heated to 60° C. for 16 h. The reaction was cooled to room temperature and concentrated under vacuum. The residue was taken up in DMSO and purified by Gilson preparatory HPLC (without TFA) to give the title compound (0.0417 g, 59.6%). EI-MS m/z 451 (M$^+$) Rt (1.20 min).

Example 25

Preparation of 4-[cyano(diphenyl)methyl]-1-{2-[(phenylmethyl)oxy]ethyl}-1-azoniabicyclo[2.2.1]heptane bromide Following the general procedure outlined in Example 24, 1-azabicyclo[2.2.1]hept-4-yl(diphenyl)acetonitrile (0.044 g, 0.152 mmol) and 2-bromoethyl phenylmethyl ether (0.040 mL, 0.253 mmol) in 2CH$_3$CN/3CHCl$_3$ (3.5 mL) were reacted to give the desired product (0.0281 g, 37.0%). EI-MS m/z 423 (M$^+$) Rt (2.02 min).

Example 26

Preparation of 4-[cyano(diphenyl)methyl]-1-ethyl-1-azoniabicyclo[2.2.1]heptane bromide Following the general procedure outlined in Example 24, 1-azabicyclo[2.2.1]hept-4-yl(diphenyl)acetonitrile (0.044 g, 0.152 mmol) and bromoethane (0.020 mL, 0.268 mmol) in 2CH$_3$CN/3CHCl$_3$ (3.5 mL) were reacted to give the desired product (0.0178 g, 29.7%). EI-MS m/z 317 (M$^+$) Rt (1.53 rain).

Example 27

Preparation of 4-[cyano(diphenyl)methyl]-1-[3-(methyloxy)propyl]-1-azoniabicyclo[2.2.1]heptane bromide Following the general procedure outlined in Example 24, 1-azabicyclo[2.2.1]hept-4-yl(diphenyl)acetonitrile (0.044 g, 0.152 mmol) and 3-bromopropyl methyl ether (0.035 g, 0.229 mmol) in 2CH$_3$CN/3CHCl$_3$ (3.5 mL) were reacted to give the desired product (0.0277 g, 41.3%). EI-MS m/z 361 (M$^+$) Rt (1.58 min).

Example 28

Preparation of 4-[cyano(diphenyl)methyl]-1-(3-phenylpropyl)-1-azoniabicyclo[2.2.1]heptane bromide Following the general procedure outlined in Example 24, 1-azabicyclo[2.2.1]hept-4-yl(diphenyl)acetonitrile (0.044 g, 0.152 mmol) and (3-bromopropyl)benzene (0.035 mL, 0.230 mmol) in 2CH$_3$CN/3CHCl$_3$ (3.5 mL) were reacted to give the desired product (0.0328 g, 44.3%). EI-MS m/z 407 (M$^+$) Rt (1.82 min).

Example 29

Preparation of 4-[cyano(diphenyl)methyl]-1-hexyl-1-azoniabicyclo[2.2.1]heptane bromide Following the general procedure outlined in Example 24, 1-azabicyclo[2.2.1]hept-4-yl(diphenyl)acetonitrile (0.044 g, 0.152 mmol) and 1-bromohexane (0.035 mL, 0.249 mmol) in 2CH$_3$CN/3CHCl$_3$ (3.5 mL) were reacted to give the desired product (0.0306 g, 44.3%). EI-MS m/z 373 (M$^+$) Rt (1.83 min).

Example 30

Preparation of 4-[cyano(diphenyl)methyl]-1-(2-hydroxyethyl)-1-azoniabicyclo[2.2.1]heptane bromide Following the general procedure outlined in Example 24, 1-azabicyclo[2.2.1]hept-4-yl(diphenyl)acetonitrile (0.044 g, 0.152 mmol) and 3-bromo-1-propanol (0.020 mL, 0.282 mmol) in 2CH$_3$CN/3CHCl$_3$ (3.5 mL) were reacted to give the desired product (0.0196 g, 31.1%). EI-MS m/z 333 (M$^+$) Rt (1.43 min).

Example 31

Preparation of 4-[cyano(diphenyl)methyl]-1-(cyclohexylmethyl)-1-azoniabicyclo[2.2.1]heptane bromide Following the general procedure outlined in Example 24, 1-azabicyclo[2.2.1]hept-4-yl(diphenyl)acetonitrile (0.044 g, 0.152 mmol) and (bromomethyl)cyclohexane (0.030 mL, 0.215 mmol) in 2CH$_3$CN/3CHCl$_3$ (3.5 mL) were reacted to give the desired product (0.0172 g, 24.2%). EI-MS m/z 385 (M$^+$) Rt (1.82 min).

Example 32

Preparation of 4-[cyano(diphenyl)methyl]-1-[2-(1H-indol-2-yl)ethyl]-1-azoniabicyclo[2.2.1]heptane bromide Following the general procedure outlined in Example 24, 1-azabicyclo[2.2.1]hept-4-yl(diphenyl)acetonitrile (0.044 g, 0.152 mmol) and 2-(2-bromoethyl)-1H-indole (0.0494 g, 0.220 mmol) in 2CH$_3$CN/3CHCl$_3$ (3.5 mL) were reacted to give the desired product (0.0340 g, 43.4%). EI-MS m/z 432 (M$^+$) Rt (1.94 min).

Example 33

Preparation of 4-[cyano(diphenyl)methyl]-1-(3-cyanopropyl)-1-azoniabicyclo[2.2.1]heptane bromide Following the general procedure outlined in Example 24, 1-azabicyclo[2.2.1]hept-4-yl(diphenyl)acetonitrile (0.044 g, 0.152 mmol) and 4-bromobutanenitrile (0.025 mL, 0.252 mmol) in 2CH$_3$CN/3CHCl$_3$ (3.5 mL) were reacted to give the desired product (0.0360 g, 54.1%). EI-MS m/z 356 (M$^+$) Rt (1.57 min).

Example 34

Preparation of 4-[cyano(diphenyl)methyl]-1-[3-(phenyloxy)propyl]-1-azoniabicyclo[2.2.1]heptane bromide Following the general procedure outlined in Example 24, 1-azabicyclo[2.2.1]hept-4-yl(diphenyl)acetonitrile (0.19 g, 0.658 mmol) and 3-bromopropyl phenyl ether (0.17 mL, 1.07 mmol) in 2CH$_3$CN/3CHCl$_3$ (15 mL) were reacted to give the desired product (0.146 g, 45%). EI-MS m/z 423 (M+), $^1$H NMR (400 MHz, CD$_3$OD) δ 7.5 (m, 4H), δ 7.35 (m, 3H), δ 7.3-7.2 (m, 4H), δ 6.9 (m, 4H), δ 4.07 (m, 3H), 3.8-3.7 (m, 2H), δ 3.62 (m, 5H), δ 3.6-2.5 (m, 2H), δ 2.4-2.3 (m, 2H), δ 2.3-2.1 (m, 5H).

| Abbreviations | |
|---|---|
| Ar | Argon |
| DCE | 1,2-Dichloroethane |
| DCM | Dichloromethane |
| DMF | Dimethylformamide |
| DMSO | Dimethylsulfoxide |
| EI-MS | Electrospray ionization-mass spectrometry |
| HPLC | High pressure liquid chromatography |
| LC | Liquid chromatography |
| LDA | Lithium Diisopropyl Amide |
| MS | Mass spectrometry |
| NMR | Nuclear magnetic resonance |
| Rt | Retention time |
| rt | room temperature |
| SPE | Solid phase extraction |
| TEA | Triethylamine |
| TFA | Trifluoroacetic acid |
| THF | Tetrahydrofuran |

BIOLOGICAL EXAMPLES

The inhibitory effects of compounds at the M$_3$ mAChR of the present invention are determined by the following in vitro and in vivo functional assays:

Analysis of Inhibition of Receptor Activation by Calcium Mobilization:

Stimulation of mAChRs expressed on CHO cells were analyzed by monitoring receptor-activated calcium mobilization as previously described (H. M. Sarau et al, 1999. *Mol. Pharmacol.* 56, 657-663). CHO cells stably expressing M$_3$ mAChRs were plated in 96 well black wall/clear bottom plates. After 18 to 24 hours, media was aspirated and replaced with 100l of load media (EMEM with Earl's salts, 0.1% RIA-grade BSA (Sigma, St. Louis Mo.), and 4 µM Fluo-3-acetoxymethyl ester fluorescent indicator dye (Fluo-3 AM, Molecular Probes, Eugene, Oreg.) and incubated 1 hr at 37° C. The dye-containing media was then aspirated, replaced with fresh media (without Fluo-3 AM), and cells were incubated for 10 minutes at 37° C. Cells were then washed 3 times and incubated for 10 minutes at 37° C. in 100 µl of assay buffer (0.1% gelatin (Sigma), 120 mM NaCl, 4.6 mM KCl, 1 mM KH$_2$ PO$_4$, 25 mM NaH CO$_3$, 1.0 mM CaCl$_2$, 1.1 mM MgCl$_2$, 11 mM glucose, 20 mM HEPES (pH 7.4)). 50 µl of compound ($1\times10^{-11}$-$1\times10^{-5}$ M final in the assay) was added and the plates were incubated for 10 min. at 37° C. Plates were then placed into a fluorescent light intensity plate reader (FLIPR, Molecular Probes) where the dye loaded cells were exposed to excitation light (488 nm) from a 6 watt argon laser. Cells were activated by adding 50 µl of acetylcholine (0.1-10 nM final), prepared in buffer containing 0.1% BSA, at a rate of 50 µl/sec. Calcium mobilization, monitored as change in cytosolic calcium concentration, was measured as change in 566 nm emission intensity. The change in emission intensity is directly related to cytosolic calcium levels. The emitted fluorescence from all 96 wells is measured simultaneously using a cooled CCD camera. Data points are collected every second. This data was then plotting and analyzed using GraphPad PRISM software.

Methacholine-Induced Bronchoconstriction—Potency and Duration of Action

Airway responsiveness to methacholine was determined in awake, unrestrained Balb C mice (n=6 each group). Barometric plethysmograph was used to measure enhanced pause (Penh), a unitless measure that has been shown to correlate with the changes in airway resistance that occur during bronchial challenge with methacholine (2). Mice were pre-treated with 50 µl of compound (0.003-10 µg/mouse) in 50 µl of vehicle (10% DMSO) intranasally (i.n.) and were then placed in the plethysmography chamber a given amount of time following drug administration (15 min-96 h). For potency determination, a dose response to a given drug was performed, and all measurements were taken 15 min following i.n. drug administration. For duration of action determination, measurements were taken anywhere from 15 min to 96 hours following i.n. drug administration.

Once in the chamber, the mice were allowed to equilibrate for 10 min before taking a baseline Penh measurement for 5 minutes. Mice were then challenged with an aerosol of methacholine (10 mg/ml) for 2 minutes. Penh was recorded continuously for 7 min starting at the inception of the methacholine aerosol, and continuing for 5 minutes afterward. Data for each mouse were analyzed and plotted by using GraphPad PRISM software. This experiment allows the determination of duration of activity of the administered compound.

The present compounds are useful for treating a variety of indications, including but not limited to respiratory-tract disorders such as chronic obstructive lung disease, chronic bronchitis, asthma, chronic respiratory obstruction, pulmonary fibrosis, pulmonary emphysema, and allergic rhinitis.

Evaluation of Potency and Duration of Action in Isolated Guinea Pig Trachea

Tracheae were removed from adult male Hartely guinea pigs (Charles River, Raleigh, N.C.; 400-600 grams) and placed into modified Krebs-Henseleit solution. Composition of the solution was (mM): NaCl 113.0, KCl 4.8, CaCl$_2$ 2.5, KH$_2$PO$_4$ 1.2, MgSO$_4$ 1.2, NaHCO$_3$ 25.0 and dextrose 11.0. which was gassed with 95% O$_2$: 5% CO$_2$ and maintained at 37° C. Each trachea was cleaned of adherent tissue and opened lengthwise. Epithelium was removed by gently rubbing the luminal surface with a cotton-tipped applicator. Individual strips were cut, approximately 2 cartilage rings in width, and suspended via silk suture in 10-ml water-jacketed organ baths containing Krebs-Henseleit solution and connected to Grass FT03C force-displacement transducers. Mechanical responses were recorded isometrically by MP100WS/Acknowledge data acquisition system (BIOPAC Systems, Goleta, Calif., www.biopac.com) run on Apple G4 computers. The tissues were equilibrated under a resting tension of 1.5 g, determined to be optimal by length-tension evaluation, and washed with Krebs-Henseleit solution every 15 minutes for one hour. After the equilibration period pulmonary tissues were contracted with 10 uM carbachol until reaching plateau, which served as a reference contraction for data analysis. Tissues were then rinsed every 15 minutes over 1 hour until reaching baseline tone. The preparations were then left for at least 30 minutes before the start of the experiment.

Concentration-response curves were obtained by a cumulative addition of carbachol in half-log increments (Van Rossum, 1963, Arch. Int. Pharmacodyn., 143:299), initiated at 1 nM. Each concentration was left in contact with the preparation until the response plateaued before the addition of the subsequent carbachol concentration. Paired tissues were exposed to mAChR antagonist compounds or vehicle for 30 min before carbachol cumulative concentration-response curves were generated. All data is given as mean standard error of the mean (s.e.m.) with n being the number of different animals.

For superfusion (duration of action) studies, the tissues were continuously superfused with Krebs-Henseleit solution at 2 ml/min for the duration of the experiment. Stock solutions of agonist and antagonist were infused (0.02 ml/min) via 22-gauge needle inserted into the superfusion tubing. Mechanical responses were recorded isometrically using a commercially-available data acquisition system (MP100WS/Acknowledge; BIOPAC Systems, Goleta, Calif., www.biopac.com) interfaced with a Macintosh G4 computer (Apple, Cupertino, Calif. www.apple.com). The tissues were suspended under an optimal resting tension of 1.5 g. After a 60 min equilibration period, the tissues were contracted with carbachol (1 uM) for the duration of the experiment. Upon reaching a sustained contraction isoproterenol (10 uM) was administered to maximally relax the tissue, and this change served as a reference. Isoproterenol exposure was halted and the carbachol-induced tension allowed to recover. Muscarinic receptor antagonists infused at a single concentration per tissue until a sustained level of inhibition was attained. The compound was then removed and, once again, the carbachol-induced tension was allowed to recover.

The following parameters were determined for each concentration of antagonist, and expressed as the mean ±S.E.M. for n individual animals. Inhibition of the carbachol-induced contraction was expressed as a percent of the reference response (isoproterenol) and the time required to reach one-half of this relaxation was measured (onset of response). The tension recovery following removal of the compound was determined as was the time required to reach one-half of the maximum tension recovery (offset of response). At 60 and 180 minutes after removal of the antagonist the remaining level of inhibition was determined and expressed as a percent of the isoproterenol reference.

Antagonist concentration-response curves were obtained by plotting the maximal relaxation data at 0, 60 and 180-min following antagonist withdrawal. Recovery, termed shift, was calculated from the ratio of the 0-min inhibition curve $IC_{50}$ and the concentration of compound yielding a similar tension recovery at 60 and 180 minutes.

Halftimes for onset and offset of response were plotted vs. corresponding concentration and the data were fit with non-linear regression. These values were extrapolated at the $IC_{50}$ (determined from the inhibition concentration-response curve) and designated $Ot_{50}$ (time required, at the $IC_{50}$ concentration, to reach half of the onset response) and Rt50 (time required, at the $IC_{50}$ concentration, to reach half of the recovery response).

Formulation Administration

Accordingly, the present invention further provides a pharmaceutical formulation comprising a compound of formula (I), or a pharmaceutically acceptable salt, solvate, or physiologically functional derivative (e.g., salts and esters) thereof, and a pharmaceutically acceptable carrier or excipient, and optionally one or more other therapeutic ingredients.

Hereinafter, the term "active ingredient" means a compound of formula (I), or a pharmaceutically acceptable salt, solvate, or physiologically functional derivative thereof.

Compounds of formula (I) will be administered via inhalation via the mouth or nose.

Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di- or poly-saccharides (e.g., lactose or starch), organic or inorganic salts (e.g., calcium chloride, calcium phosphate or sodium chloride), polyalcohols (e.g., mannitol), or mixtures thereof, alternatively with one or more additional materials, such additives included in the blend formulation to improve chemical and/or physical stability or performance of the formulation, as discussed below, or mixtures thereof. Use of lactose is preferred. Each capsule or cartridge may generally contain between 20 µg-10 mg of the compound of formula (I) optionally in combination with another therapeutically active ingredient. Alternatively, the compound of the invention may be presented without excipients, or may be formed into particles comprising the compound, optionally other therapeutically active materials, and excipient materials, such as by co-precipitation or coating.

Suitably, the medicament dispenser is of a type selected from the group consisting of a reservoir dry powder inhaler (RDPI), a multi-dose dry powder inhaler (MDPI), and a metered dose inhaler (MDI).

By reservoir dry powder inhaler (RDPI) it is meant as an inhaler having a reservoir form pack suitable for comprising multiple (un-metered doses) of medicament in dry powder form and including means for metering medicament dose from the reservoir to a delivery position. The metering means may for example comprise a metering cup or perforated plate, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose pack containing (or otherwise carrying) multiple, define doses (or parts thereof) of medicament. In a preferred aspect, the carrier has a blister pack form, but it could also, for example, comprise a capsule-based pack form or a carrier onto which medicament has been applied by any suitable process including printing, painting and vacuum occlusion.

The formulation can be pre-metered (e.g. as in Diskus, see GB 2242134 or Diskhaler, see GB 2178965, 2129691 and 2169265) or metered in use (e.g. as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

In one aspect, the multi-dose pack is a blister pack comprising multiple blisters for containment of medicament in dry powder form. The blisters are typically arranged in regular fashion for ease of release of medicament therefrom.

In one aspect, the multi-dose blister pack comprises plural blisters arranged in generally circular fashion on a disk-form blister pack. In another aspect, the multi-dose blister pack is elongate in form, for example comprising a strip or a tape.

Preferably, the multi-dose blister pack is defined between two members peelably secured to one another. U.S. Pat. Nos. 5,860,419, 5,873,360 and 5,590,645 describe medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants e.g. oleic acid or lecithin and cosolvents e.g. ethanol. Pressurised formulations will generally be retained in a canister (e.g. an aluminium canister) closed with a valve (e.g. a metering valve) and fitted into an actuator provided with a mouthpiece.

Medicaments for administration by inhalation desirably have a controlled particle size. The optimum aerodynamic particle size for inhalation into the bronchial system for localized delivery to the lung is usually 1-10 µm, preferably 2-5 µm. The optimum aerodynamic particle size for inhalation into the alveolar region for achieving systemic delivery to the lung is approximately 0.5-3 µm, preferably 1-3 µm. Particles having an aerodynamic size above 20 µm are generally too large when inhaled to reach the small airways. Average aerodynamic particle size of a formulation may measured by, for example cascade impaction. Average geometric particle size may be measured, for example by laser diffraction, optical means.

To achieve a desired particle size, the particles of the active ingredient as produced may be size reduced by conventional means e.g. by controlled crystallization, micronisation or nanomilling. The desired fraction may be separated out by air classification. Alternatively, particles of the desired size may be directly produced, for example by spray drying, controlling the spray drying parameters to generate particles of the desired size range. Preferably, the particles will be crystalline, although amorphous material may also be employed where desirable. When an excipient such as lactose is employed, generally, the particle size of the excipient will be much greater than the inhaled medicament within the present invention, such that the "coarse" carrier is non-respirable. When the excipient is lactose it will typically be present as milled lactose, wherein not more than 85% of lactose particles will have a MMD of 60-90 µm and not less than 15% will have a MMD of less than 15 µm. Additive materials in a dry powder blend in addition to the carrier may be either respirable, i.e., aerodynamically less than 10 microns, or non-respirable, i.e., aerodynamically greater than 10 microns.

Suitable additive materials which may be employed include amino acids, such as leucine; water soluble or water insoluble, natural or synthetic surfactants, such as lecithin (e.g., soya lecithin) and solid state fatty acids (e.g., lauric, palmitic, and stearic acids) and derivatives thereof (such as salts and esters); phosphatidylcholines; sugar esters. Additive materials may also include colorants, taste masking agents (e.g., saccharine), anti-static-agents, lubricants (see, for example, Published PCT Patent Appl. No. WO 87/905213, the teachings of which are incorporated by reference herein), chemical stabilizers, buffers, preservatives, absorption enhancers, and other materials known to those of ordinary skill.

Sustained release coating materials (e.g., stearic acid or polymers, e.g. polyvinyl pyrolidone, polylactic acid) may also be employed on active material or active material containing particles (see, for example, Patent Nos. U.S. Pat. No. 3,634,582, GB 1,230,087, GB 1,381,872, the teachings of which are incorporated by reference herein).

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Preferred unit dosage formulations are those containing an effective dose, as herein before recited, or an appropriate fraction thereof, of the active ingredient.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to Formula (I):

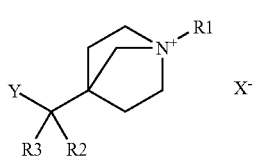

(I)

wherein:

Y is OH or CN;

R1 is C1-15 alkyl, cyanosubstituted C1-15 alkyl, halosubstituted C1-15 alkyl, —C1-15 alkyl cycloalkyl, C2-15 alkenyl, hydroxy substituted C1-15 alkyl, -C2-15 alkyl aryl, -C2-15 alkyl heteroaryl, —(CH2)qOC(O)Ra, —(CH2)qORc or

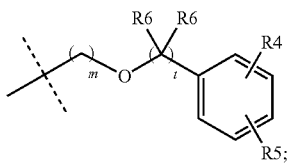

R4 and R5 are, independently, selected from hydrogen, halogen, C1-4 alkyl, aryl, C1-4 alkyl aryl, cyano, nitro, or (CH2)pORb, or R4 and R5 together may form a 5 to 6 membered saturated or unsaturated ring;

R6 is selected from the group consisting of hydrogen, and C1-4 alkyl;

m is an integer having a value of 1 to 15;

R2 and R3 are, independently, selected from the group consisting of aryl and heteroaryl;

Ra is hydrogen, C1-15 alkyl, C1-15 alkoxy or aryl;

Rb is hydrogen, or C1-4 alkyl;

Rc is selected from hydrogen, C1-15 alkyl, C1-15 alkoxy, or heterocyclic;

p is 0 or an integer having a value of 1 to 4;

q is an integer having a value of 1 to 5;

t is 0 or an integer having a value of 1 to 5; and

X— is a physiologically acceptable anion.

2. A compound according to claim 1 wherein:

Y is OH or CN;

R1 is C7-12 alkyl, or

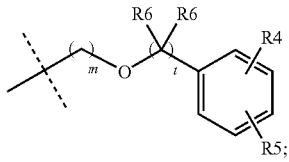

R4 and R5 are, independently, selected from the group consisting of hydrogen, halogen, hydroxyl, methoxy, cyano, nitro, or R4 and R5 together may form 6 membered saturated ring;

R6 is hydrogen;

m is an integer having a value of 1 to 5;

R2 and R3 are, independently, selected from the group consisting of aryl and heteroaryl;

t is 0 or an integer having a value of 1 to 5;

X— is selected from the group consisting of chloride, bromide, iodide, hydroxide, sulfate, nitrate, phosphate, acetate, trifluoroacetate, fumarate, citrate, tartrate, oxalate, succinate, mandelate, methanesulfonate and p-toluenesulfonate.

3. A compound selected from the group consisting of:

4-[hydroxy(diphenyl)methyl]-1-{2-[(phenylmethyl)oxy]ethyl}-1-azoniabicyclo[2.2.1]heptane bromide;

4-[hydroxy(diphenyl)methyl]-1-(2-phenylethyl)-1-azoniabicyclo[2.2.1]heptane bromide;

1-ethyl-4-[hydroxy(diphenyl)methyl]-1-azoniabicyclo[2.2.1]heptane bromide;

4-[hydroxy(diphenyl)methyl]-1-nonyl-1-azoniabicyclo[2.2.1]heptane bromide;

4-[hydroxy(diphenyl)methyl]-1-[2-(methyloxy)ethyl]-1-azoniabicyclo[2.2.1]heptane bromide;

4-[hydroxy(diphenyl)methyl]-1-[4-(phenyloxy)butyl]-1-azoniabicyclo[2.2.1]heptane bromide;

4-[hydroxy(diphenyl)methyl]-1-{3-[(phenylmethyl)oxy]propyl}-1-azoniabicyclo[2.2.1]heptane bromide;

1-hexyl-4-[hydroxy(diphenyl)methyl]-1-azoniabicyclo[2.2.1]heptane bromide;

4-[hydroxy(diphenyl)methyl]-1-{4-[(phenylmethyl)oxy]butyl}-1-azoniabicyclo[2.2.1]heptane bromide;

1-(cyclohexylmethyl)-4-[hydroxy(diphenyl)methyl]-1-azoniabicyclo[2.2.1]heptane bromide;

1-{3-[(4-bromophenyl)oxy]propyl}-4-[hydroxy(diphenyl)methyl]-1-azoniabicyclo[2.2.1]heptane bromide;

4-[hydroxy(diphenyl)methyl]-1-{3-[(4-nitrophenyl)oxy]propyl}-1-azoniabicyclo[2.2.1]heptane bromide;

4-[hydroxy(diphenyl)methyl]-1-[3-(2-naphthalenyloxy)propyl]-1-azoniabicyclo[2.2.1]heptane bromide;

1-{3-[(3-chlorophenyl)oxy]propyl}-4-[hydroxy(diphenyl)methyl]-1-azoniabicyclo[2.2.1]heptane bromide;

1-(5-hexen-1-yl)-4-[hydroxy(diphenyl)methyl]-1-azoniabicyclo[2.2.1]heptane bromide;

4-[hydroxy(diphenyl)methyl]-1-(6-hydroxyhexyl)-1-azoniabicyclo[2.2.1]heptane bromide;

4-[hydroxy(diphenyl)methyl]-1-[3-(phenyloxy)propyl]-1-azoniabicyclo[2.2.1]heptane bromide;

4-[cyano(diphenyl)methyl]-1-(phenylmethyl)-1-azoniabicyclo[2.2.1]heptane bromide;

4-[cyano(diphenyl)methyl]-1-{2-[(phenylmethyl)oxy]ethyl}-1-azoniabicyclo[2.2.1]heptane bromide;

4-[cyano(diphenyl)methyl]-1-ethyl-1-azoniabicyclo[2.2.1]heptane bromide;

4-[cyano(diphenyl)methyl]-1-(3-phenylpropyl)-1-azoniabicyclo[2.2.1]heptane bromide;

4-[cyano(diphenyl)methyl]-1-hexyl-1-azoniabicyclo[2.2.1]heptane bromide;

4-[cyano(diphenyl)methyl]-1-(2-hydroxyethyl)-1-azoniabicyclo[2.2.1]heptane bromide;

4-[cyano(diphenyl)methyl]-1-(cyclohexylmethyl)-1-azoniabicyclo[2.2.1]heptane bromide;

4-[cyano(diphenyl)methyl]-1-[2-(1H-indol-2-yl)ethyl]-1-azoniabicyclo[2.2.1]heptane bromide;

4-[cyano(diphenyl)methyl]-1-(3-cyanopropyl)-1-azoniabicyclo[2.2.1]heptane bromide; and 4-[cyano(diphenyl)methyl]-1-[3-(phenyloxy)propyl]-1-azoniabicyclo[2.2.1]heptane bromide.

4. A pharmaceutical composition comprising a compound according to claim 1 and a pharmaceutically acceptable carrier.

5. The compound according to claim 1 wherein Y is CN.

6. The compound according to claim 5 wherein R2 and R3 are both phenyl.

7. The compound according to claim 6 wherein R4, R5, and R6 are all hydrogen.

8. The compound according to claim 1 wherein R2 and R3 are both phenyl.

9. A pharmaceutical composition comprising a compound according to claim 3 and a pharmaceutically acceptable carrier.

10. The compound according to claim 2 wherein Y is CN.

11. The compound according to claim 1 wherein X— is bromide.

12. The compound according to claim 1 wherein Y is OH.

13. The compound according to claim 12 wherein R2 and R3 are both phenyl.

14. The compound according to claim 13 wherein R4, R5, and R6 are all hydrogen.

15. The compound according to claim 2 wherein Y is OH.

16. The compound according to claim 15 wherein R2 and R3 are both phenyl.

17. The compound according to claim 15 wherein R4, R5, and R6 are all hydrogen.

18. The compound according to claim 1 wherein R1 is

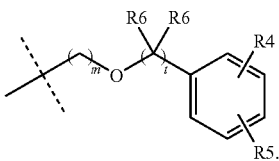

19. The compound according to claim 2 wherein R1 is

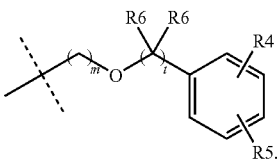

20. The compound according to claim 19 wherein Y is OH, and R2 and R3 are both phenyl.

21. The compound according to claim 20 wherein R4, R5, and R6 are all hydrogen.

22. The compound according to Claim 19 wherein R6 is hydrogen, and m is 2 and t is 1.

23. The compound according to claim 1 wherein m is 2, 3, or 4.

24. The compound according to claim 1 wherein t is 0 or 1.

25. A compound which is

4-[hydroxy(diphenyl)methyl]-1-[2-(methyloxy)ethyl]-1-azoniabicyclo[2.2.1]heptane bromide;

4-[hydroxy(diphenyl)methyl]-1-({4-[(trifluoromethyl)oxy]phenyl}methyl)-1-azoniabicyclo[2.2.1]heptane bromide;

4-[hydroxy(diphenyl)methyl]-1-[2-({[3-(methyloxy)phenyl]methyl}oxy)ethyl]-1-azoniabicyclo[2.2.1]heptane bromide;

4-[hydroxy(diphenyl)methyl]-1-{2-[(phenylcarbonyl)oxy]ethyl}-1-azoniabicyclo[2.2.1]heptane bromide;

4-[hydroxy(diphenyl)methyl]-1-{3-[(2-hydroxyphenyl)oxy]propyl}-1-azoniabicyclo[2.2.1]heptane bromide;

4-[hydroxy(diphenyl)methyl]-1-{[3-(methyloxy)phenyl]methyl}-1-azoniabicyclo[2.2.1]heptane bromide;

4-[hydroxy(diphenyl)methyl]-1-(6-hydroxyhexyl)-1-azoniabicyclo[2.2.1]heptane bromide; or 4-[cyano(diphenyl)methyl]-1-[3-(methyloxy)propyl]-1-azoniabicyclo[2.2.1]heptane bromide.

26. A pharmaceutical composition comprising a compound according to claim 25 and a pharmaceutically acceptable carrier.

* * * * *